United States Patent
Yan et al.

(10) Patent No.: US 12,408,659 B2
(45) Date of Patent: Sep. 9, 2025

(54) DMSO-FREE CRYOPRESERVATION SOLUTION AND PREPARATION METHOD AND USE THEREOF

(71) Applicants: PEKING UNIVERSITY THIRD HOSPITAL, Beijing (CN); INSTITUTE OF CHEMISTRY, CHINESE ACADEMY OF SCIENCES, Beijing (CN)

(72) Inventors: Jie Yan, Beijing (CN); Jie Qiao, Beijing (CN); Liying Yan, Beijing (CN); Rong Li, Beijing (CN); Jianjun Wang, Beijing (CN); Shenglin Jin, Beijing (CN); Jianyong Lv, Beijing (CN)

(73) Assignees: PEKING UNIVERSITY THIRD HOSPITAL, Beijing (CN); INSTITUTE OF CHEMISTRY, CHINESE ACADEMY OF SCIENCES, Beijing (CN)

(*) Notice: Subject to any disclaimer, the term of this patent is extended or adjusted under 35 U.S.C. 154(b) by 1009 days.

(21) Appl. No.: 17/594,202

(22) PCT Filed: Mar. 2, 2020

(86) PCT No.: PCT/CN2020/077473
§ 371 (c)(1),
(2) Date: Oct. 6, 2021

(87) PCT Pub. No.: WO2020/207151
PCT Pub. Date: Oct. 15, 2020

(65) Prior Publication Data
US 2022/0167610 A1    Jun. 2, 2022

(30) Foreign Application Priority Data

Apr. 9, 2019  (CN) .......................... 201910281978.2
Apr. 9, 2019  (CN) .......................... 201910281986.7

(51) Int. Cl.
| | | |
|---|---|---|
| *A01N 1/125* | (2025.01) | |
| *C07K 5/062* | (2006.01) | |
| *C07K 5/072* | (2006.01) | |
| *C07K 5/078* | (2006.01) | |
| *C07K 5/083* | (2006.01) | |

(52) U.S. Cl.
CPC ............ *A01N 1/125* (2025.01); *C07K 5/0606* (2013.01); *C07K 5/06095* (2013.01); *C07K 5/06165* (2013.01); *C07K 5/0806* (2013.01); *C07K 5/081* (2013.01)

(58) Field of Classification Search
CPC ................................. A01N 1/12; A01N 1/125
See application file for complete search history.

(56) References Cited

FOREIGN PATENT DOCUMENTS

| CN | 101250499 A | 8/2008 | |
|---|---|---|---|
| CN | 108207930 A | 6/2018 | |
| CN | 109221082 A | 1/2019 | |
| WO | 9110361 A1 | 7/1991 | |
| WO | WO-0016619 A1 * | 3/2000 | ............... A01N 1/02 |
| WO | 2018191411 A1 | 10/2018 | |

OTHER PUBLICATIONS

Translation of CN108207930 (original document is cited in IDS) (Year: 2016).*
Yamasaki J, Iwatani C, Tsuchiya H, Okahara J, Sankai T, Torii R. Vitrification and transfer of cynomolgus monkey (*Macaca fascicularis*) embryos fertilized by intracytoplasmic sperm injection. Theriogenology. Jul. 1, 2011;76(1):33-8. (Year: 2011).*
Heo YS, Nagrath S, Moore AL, Zeinali M, Irimia D, Stott SL, Toth TL, Toner M. "Universal" vitrification of cells by ultra-fast cooling. Technology (Singap World Sci). Mar. 2015;3(1):64-71. doi: 10.1142/S2339547815500053. PMID: 25914896; PMCID: PMC4404302. (Year: 2015).*
Tetsuya Tanigushi, Yoshimitsu Shirai, Kazuo Yamaura, Shuji Matsuzawa, Blends between two types of poly(vinyl alcohol)s with different syndiotacticities, Polymer, vol. 35, Issue 9, 1994, pp. 1970-1976, ISSN 0032-3861, (Year: 1994).*
Huang, Fengling et al.; Quick Freezing of Bovine IVF Embryos, Journal of Guangxi Agricultural University, vol. 13, No. 1, Mar. 30, 1994, ISSN: 1005-201, the abstract.

* cited by examiner

*Primary Examiner* — Fereydoun G Sajjadi
*Assistant Examiner* — Qinhua Gu
(74) *Attorney, Agent, or Firm* — NKL Law; Allen Xue

(57) ABSTRACT

A cryopreservation solution contains 0.01-50.0 g of bionic ice control materials, 5.0-30 mL of polyols, 1-30 g of water-soluble sugar, and 0-30 mL of serum, and a buffer in every 100 mL of the cryopreservation solution. It does not contain DMSO. When being used for the cryopreservation of mouse oocytes and embryos, the solution may achieve the same or an even higher cell and tissue survival rate and functional expression stability as or than a commercial cryopreservation solution (containing 15% DMSO), and has high preservation efficiency. The cryopreservation solution without DMSO or serum reduces parasitic biological contaminants in the commercial cryopreservation solution containing serum currently used in clinical practice.

20 Claims, 5 Drawing Sheets

DMSO-FREE CRYOPRESERVATION SOLUTION AND PREPARATION METHOD AND USE THEREOF

CROSS-REFERENCE TO RELATED APPLICATIONS

The present application is a U.S. national entry of PCT International Application No. PCT/CN2020/077473, filed Mar. 2, 2020, which claims priority to Chinese Patent Application No. 201910281978.2, filed to China National Intellectual Property Administration on Apr. 9, 2019, entitled "DMSO-FREE CRYOPRESERVATION SOLUTION AND PREPARATION METHOD THEREOF", and Chinese Patent Application No. 201910281986.7, filed to China National Intellectual Property Administration on Apr. 9, 2019, entitled "PEPTIDE COMPOUND AND CRYO-PRESERVATION SOLUTION COMPRISING SAME", which are incorporated herein by reference in their entirety.

TECHNICAL FIELD

The present invention relates to the technical field of biomedical materials, and particularly to a DMSO-free cryopreservation solution and a preparation method thereof.

BACKGROUND

The cryopreservation technology has become one of indispensable research methods in the field of natural science since its advent, and has been widely applied, With the improvement of living standards and the development of medical technology, the cryopreservation of human germ cells (sperms and oocytes), gonad tissues and the like has become an important means of fertility preservation. In addition, as the world population ages, the need for cryopreservation of donated human cells, tissues or organs that can be used for regenerative medicine and organ transplantation is growing fast. Therefore, how to efficiently cryopreserve precious cells, tissues, and organs has become an important topic in the field of life sciences.

Currently, the most commonly available cryopreservation method is vitrification. Although the vitrification technology can allow liquid inside and outside a cell to be directly vitrified in the rapid freezing process so as to avoid the damage resulting from the formation of ice crystals in the freezing process, cryopreservation reagents of the prior art are not effective in controlling the growth and recrystallization of the ice crystals in the thawing process and thus damage the cell. Dimethyl sulfoxide (DMSO) is a commonly used co-solvent and permeation type cell cryopreservation agent for in vitro cell culture. However, DMSO has adverse side effects in clinical trials and also exhibits high cytotoxicity. Different types of cells have different sensitivities to a DMSO concentration, which leads to the toxic and side effects of cryopreservation reagents taking DMSO as the main protective agent component on cells. The application of the cryopreservation reagents thus is limited. At present, vitrification usually uses a high concentration (≥15%) of DMSO, which has serious impacts on the survival rate and even the safety (of offspring) and function expression of cryopreserved objects after recovering. In conclusion, the currently used cryopreservation reagents have the problems of having no capability of effectively controlling the growth and recrystallization of ice crystals in the thawing process and being high in toxicity.

SUMMARY

In order to overcome the aforementioned drawbacks of the prior art, the present invention provides a DMSO-free cryopreservation solution and a preparation method thereof.

The present invention provides the following technical solution:

a DMSO-free cryopreservation solution comprising, per 100 mL in volume, 0.01-50.0 g of a biomimetic ice growth inhibition material, 5.0-45 mL of a polyalcohol, a water-soluble saccharide at 0.1-1 mol $L^{-1}$, 0-30 mL of serum and the balance of a buffer, wherein the biomimetic ice growth inhibition material is selected from polyvinyl alcohol (PVA) and/or an amino acid biomimetic ice growth inhibition material, and the cryopreservation solution is free of dimethyl sulfoxide (DMSO).

According to the present invention, the amino acid biomimetic ice growth inhibition material is selected from one or two or more of a polyamine acid (with a degree of polymerization ≥2, preferably 8-40, such as 8, 15 or 20 etc.), an amino acid and a peptide compound.

According to the present invention, the peptide compound is a polypeptide (preferably a peptide consisting of 2 to 8 different amino acids, such as a dipeptide, a tripeptide or a tetrapeptide), a glycopeptide derivative, or a compound of formula (I):

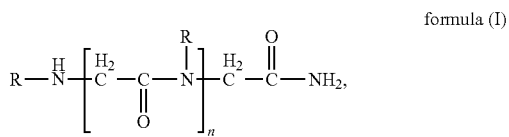

formula (I)

wherein R is selected from substituted or unsubstituted alkyl, and the substituent may be selected from —OH, —NH$_2$, —COOH, 13 CONH$_2$ and the like; for example, R is substituted or unsubstituted C$_{1-6}$ alkyl, and preferably R is —CH$_3$, —CH$_2$CH$_3$ or —CH$_2$CH$_2$COOH; n is an integer greater than or equal to 1 and less than or equal to 1000, and, for example, may be an integer ranging from 1 to 100. In some embodiments of the present invention, n is an integer such as 2, 3, 4, 5, 6, 7, 8, 9 or 10.

According to the present invention, the polyalcohol may be C2-5 polyalcohol, preferably C2-C3 dihydric alcohol and trihydric alcohol, and for example, any one of ethylene glycol, propylene glycol and glycerol.

According to the present invention, the water-soluble saccharide may be at least one of a non-reducing disaccharide, a water-soluble polysaccharide, a water-soluble cellulose and a glycoside, for example, selected from sucrose, trehalose, polysucrose and hydroxypropyl methylcellulose. The water-soluble saccharide can protect cell membranes and prevent cell from sedimentation.

According to the present invention, the buffer may be at least one of DPBS, hepes-buffered HTF buffer and other cell buffers.

According to the present invention, the serum can be human serum albumin or a substitute thereof, such as sodium dodecyl sulfate (SDS), for a human-derived cryopreservation object, and can be fetal bovine serum or bovine serum albumin for a non-human-derived cryopreservation object.

According to the cryopreservation solution disclosed herein, the biomimetic ice growth inhibition material may be a PVA, and the content of the PVA is 0.1-6.0 g, such as 0.5-5.0 g, and specifically, may be 1.0 g, 2.0 g, 3.0 g or 4.0 g.

According to the cryopreservation solution disclosed herein, the biomimetic ice growth inhibition material may be a polyamino acid or an amino acid, and the content of the polyamino acid or amino acid is 0.01-50 g, such as 1.5-50 g, and specifically, may be 8.0 g, 10 g, 15 g, 20 g, 30 g or 40 g.

According to the cryopreservation solution disclosed herein, the ice growth inhibition material may be a combination of a PVA and a polyamino acid, for example consists of 0.1-5.0 g of the PVA and 1.0-9.0 g of the polyamino acid.

According to the cryopreservation solution disclosed herein, the ice growth inhibition material may be a combination of a PVA and an amino acid, for example consists of 0.1-5.0 g of the PVA and 8.0-35 g of the amino acid.

According to the cryopreservation solution disclosed herein, the content of the polyalcohol is 6.0-28 mL, such as 7.0-20 mL or 10-15 mL, per 100 mL of the cryopreservation solution.

According to the cryopreservation solution disclosed herein, the content of the serum is 0.1-30 mL, such as 5.0-20 mL or 10-15 mL, per 100 mL of the cryopreservation solution.

According to the cryopreservation solution disclosed herein, the content of the serum is preferably 0 per 100 mL of the cryopreservation solution.

According to the cryopreservation solution disclosed herein, the content of the water-soluble saccharide is 0.1-1.0 mot $L^{-1}$ per 100 mL of the cryopreservation solution, such as 0.1-0.8 mol $L^{-1}$ or 0.2-0.6 mol $L^{-1}$, and specifically, such as 0.25 mol $L^{-1}$, 0.5 mol $L^{-1}$, or 1.0 mol $L^{-1}$.

According to the cryopreservation solution disclosed herein, the pH of the cryopreservation solution is 6.5-7.6, such as 6.9-7.2.

As an embodiment of the present invention, the cryopreservation solution consists of the following components per 100 mL in volume:
  0.01-6.0 g of a PVA,
  5.0-45 mL of a polyalcohol,
  0.1-30 mL of serum,
  a water-soluble saccharide at 0.1-1.0 mol $L^{-1}$ and
  the balance of a buffer.

Preferably, the cryopreservation solution consists of the following components per 100 mL in volume:
  1.0-6.0 g of PVA,
  5-30 mL, of ethylene glycol,
  0.1-20 mL of serum,
  sucrose at 0.2-0.8 mol $L^{-1}$, and
  the balance of DPBS.

As an embodiment of the present invention, the cryopreservation solution consists of the following components per 100 mL in volme:
  1.0-5.0 g of a PVA,
  10-45 mL of a polyalcohol,
  a water-soluble saccharide at 0.1-1.0 mol $L^{-1}$, and
  the balance of a buffer.

Preferably, the cryopreservation solution consists of the following components per 100 mL in volume:
  1.0-5.0 g of a PVA,
  10-30 mL of ethylene glycol,
  sucrose at 0.2-0.8 mol $L^{-1}$, and
  the balance of DPBS.

As an embodiment of the present invention, the cryopreservation solution consists of the following components per 100 mL in volume:
  2.0-50 g of an amino acid,
  0.1-6 g of a PVA,
  10-30 mL of a polyalcohol,
  a water-soluble saccharide at 0.1-1.0 mol $L^{-1}$,
  10-20 mL of serum, and
  the balance of a buffer.

Preferably, the cryopreservation solution consists of the following components per 100 mL in volume:
  5.0-18 g of L-Arg,
  3.0-12 g of L-Thr,
  1.0-6.0 g of a PVA,
  10-20 mL of ethylene glycol,
  sucrose at 0.2-0.8 mol $L^{-1}$,
  10-20 mL of serum, and
  the balance of DPBS.

As an embodiment of the present invention, the cryopreservation solution consists of the following components per 100 mL in volume:
  0.1-9.0 g of a polyamine acid,
  0.01-6.0 g of a PVA,
  10-30 mL of a polyalcohol,
  a water-soluble saccharide at 0.1-1.0 mol $L^{-1}$, and
  the balance of a buffer.

Preferably, the cryopreservation solution consists of the following components per 100 mL in volume:
  0.1-5.0 g of polyproline or polyarginine,
  1.0-6.0 g of a PVA,
  10-20 mL of ethylene glycol,
  sucrose at 0.2-0.8 mol $L^{-1}$, and
  the balance of DPBS.

The present invention also provides a preparation method of the cryopreservation solution, which comprises the following steps: dissolving a biomimetic ice growth inhibition material in DPBS, cooling to room temperature before adjusting the pH, dissolving other components except serum in the rest DPBS and mixing after cooling, and confirming or adjusting the pH again and supplementing with the buffer to reach a predetermined volume, wherein the serum is added when the cryopreservation solution is used.

The preparation method according to the present invention comprises the following steps:
  (1) dissolving a PVA in a portion of a buffer and cooling to room temperature before adjusting the pH to give a solution 1;
  (2) optionally, dissolving a polyamino acid or an amino acid in a portion of the buffer and cooling to room temperature before adjusting the pH to form a solution 2;
  (3) dissolving a water-soluble saccharide in another portion of the buffer and adding other components except serum after the water-soluble saccharide is completely dissolved to prepare a solution 3; and
  (4) mixing the solution 1, optionally the solution 2 and the solution 3 after they are cooled to room temperature, and adjusting the pH and making up to a predetermined volume with the buffer to give the cryopreservation solution.

The preparation method according to the present invention comprises the following steps:
  (1) dissolving a polyamino acid or an amino acid in a portion of a buffer and cooling to room temperature before adjusting the pH to form a solution 1;
  (2) dissolving a PVA in a portion of the buffer and cooling to room temperature before adjusting the pH to give a solution 2;
  (3) dissolving a water-soluble saccharide in another portion of the buffer and adding other components except serum after the water-soluble saccharide is completely dissolved to prepare a solution 3; and (4) mixing the solution 1, optionally the solution 2 and the solution 3 after they are cooled to room temperature, and adjusting the pH and making up to a predetermined volume with the buffer to give the cryopreservation solution.

According to the preparation method disclosed herein, when the cryopreservation solution comprises serum, the serum is added when the cryopreservation solution is used.

According to the preparation method disclosed herein, in the step (1), the PVA is dissolved by heating in a warm bath, such as heating in an oil bath or a water bath. For example, the temperature of the water bath is 60-95° C., preferably 80° C. In the step (1), the dissolving comprises a stirring step.

According to the preparation method disclosed herein, in the step (2), the dissolving is ultrasound-assisted dissolving.

Provided is a DMSO-free freezing equilibration solution comprising, per 100 mL in volume, 0-5.0 g of a PVA, 5.0-45 mL of a polyalcohol, 0-30 mL of serum and the balance of a buffer.

According to the freezing equilibration solution disclosed herein, the content of the PVA is 0.1-5.0 g, such as 0.1 g, 0.5 g, 1.0 g or 2.0 g.

According to the freezing equilibration solution disclosed herein, the content of the polyalcohol is 6.0-28 mL, such as 7.0-20 mL or 10-15 mL.

According to the freezing equilibration solution disclosed herein, the content of the serum is 0.1-30 mL, such as 5.0-2.0 mL or 10-15 mL. As an embodiment of the present invention, the content of the serum is 0.

As an embodiment of the present invention, the freezing equilibration solution comprises, per 100 mL in volume, 7.5-15 mL of a polyalcohol, 10-20 mL of serum and the balance of DPBS.

As an embodiment of the present application, the freezing equilibration solution comprises, per 100 mL in volume, 1.0-5.0 g of a PVA, 7.5-15 mL of a polyalcohol and the balance of a buffer.

In the freezing equilibration solution disclosed herein, the PVA, the polyalcohol and the serum may be selected from the types of the respective components of the cryopreservation solution.

The present invention further provides a preparation method of the freezing equilibration solution, which comprises dissolving respective components in a buffer, wherein serum is stored separately and added when the freezing equilibration solution is used.

Provided is a DMSO-free cryopreservation reagent comprising the freezing equilibration solution described above and the cryopreservation solution described above, wherein the freezing equilibrium solution and the cryopreservation solution are independently present, respectively.

According to the cryopreservation reagent disclosed herein, the content of serum in the cryopreservation solution is 0, and the freezing equilibration solution comprises, per 100 mL in volume, 1.0-5.0 g of a PVA, 7.5-15 mL of a polyalcohol and the balance of a buffer.

According to the cryopreservation reagent disclosed herein, the freezing equilibration solution comprises, per 100 mL in volume, the following components:
0-5.0 g of a PVA,
0-15 g of polyamino acid,
5.0-45 mL of a polyalcohol,
0-30 mL of serum, and
the balance of a buffer;

the cryopreservation solution comprises the following components based on a total volume of 100 mL:
0.01-6.0 g of a PVA,
0-50 g of an amino acid or a polyamino acid,
5.0-45 mL of a polyalcohol,
0-30 mL of serum,
a water-soluble saccharide at 0.1-1.0 mol L$^{-1}$, and
the balance of a buffer.

According to the present invention, the PVA is selected from one or a combination of two or more of an isotactic PVA, a syndiotactic PVA and an atactic PVA. For example, the PVA has a syndiotacticity of 15%-60%, preferably 45%-60%, such as 50%-55%.

According to the present invention, the PVA may be selected from a PVA having a molecular weight of 10-500 kDa or higher, such as 10-30 kDa, 30-50 kDa, 80-90 kDa or 200-500 kDa.

According to the present invention, the PVA may be selected from a PVA having a degree of hydrolysis of greater than 80%, such as 80%-99%, 82%-87%, 87%-89%, 89%-99% or 98%-99%.

According to the present invention, the polyamino acid may be a homopolymer (with a degree of polymerization ≥2) of at least one selected from lysine, arginine, proline, threonine, histidine, glutamic acid, aspartic acid, glycine and the like.

According to the present invention, the peptide compound is a polypeptide, which consists of two or more amino acids and can be selected from one or more of L-Thr-L-Arg (TR), L-Thr-L-Pro (TP), L-Arg-L-Thr (RT), L-Pro-L-Thr (PT), L-Thr-L-Arg-L-Thr (TRT), L-Thr-L-Pro-L-Thr (TPT) and L-Ala-L-Ala-L-Thr (AAT). These polypeptides can be synthesized using a polypeptide synthesis method known in the art, such as a solid-phase synthesis method.

According to the present invention, the glycopeptide derivative is synthesized by a saccharide and an amino acid, for example is a molecule consisting of glucono delta-lactone (GDL) and an ice-philic amino acid through chemical bonding, and for example is GDL-L-Thr, GDL-L-Gln, GDL-L-Asn, GDL-L-Phe, GDL-L-Tyr or GDL-L-Thr. The glycopeptide compound can be prepared by reacting a saccharide known in the art with an amino acid, for example by a solid-phase synthesis method or by reacting the saccharide with the amino acid in an organic solvent.

According to the present invention, the peptide compound has a structure of any one of formula (1) to formula (8):

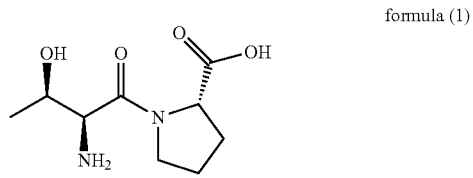

formula (1)

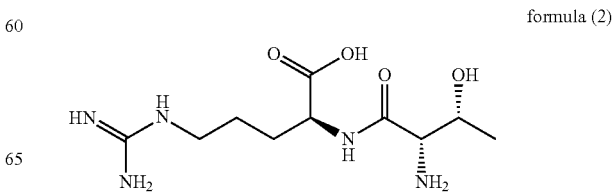

formula (2)

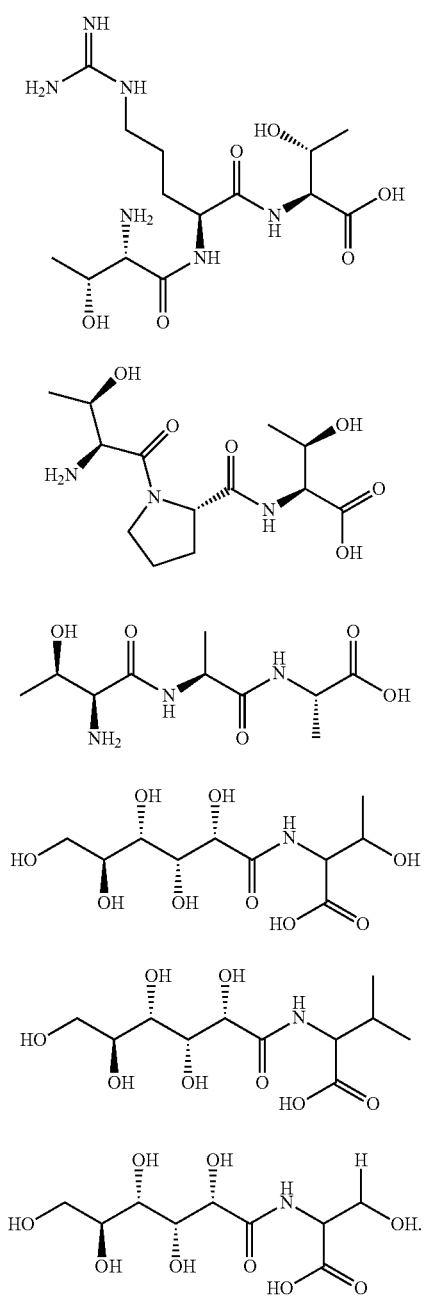

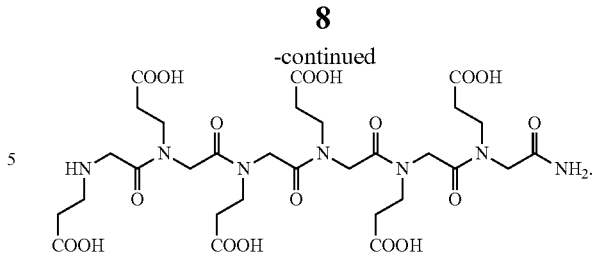

According to the present invention, the compound represented by formula (9) is prepared by using the following synthetic route:

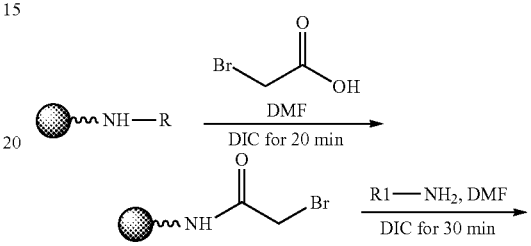

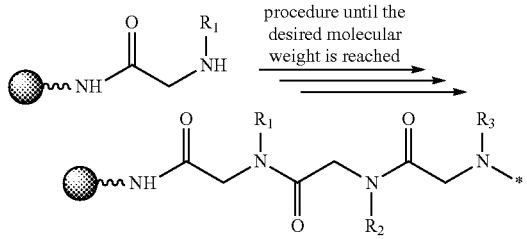

In the cryopreservation solution and the freezing equilibration solution disclosed herein, the amounts of all the components are based on a total volume of the solution of 100 mL, and the balance is a buffer.

The present invention further provides use of the cryopreservation solution in cryopreservation of various cells, organs and tissues, including cryopreservation of oocytes, embryos, various stem cells, organs and tissues, wherein the organs and the tissues include but are not limited to ovarian organs and ovarian tissues.

The present invention further provides a method for freezing and thawing cells or embryos, comprising:
(1) placing the cells or embryos into the cryopreservation solution disclosed herein to prepare a cell suspension, and freezing; and
(2) placing the frozen cells or embryos into a thawing solution for thawing and recovering.

According to the method for freezing and recovering disclosed herein, the cells or the embryos are placed into the equilibration solution for equilibration before being placed into the cryopreservation solution.

The present invention further provides a method of cryopreservation of stem cells, in which the microdroplet method is employed. For example, the method of cryopreservation of stem cells comprises the following steps: adding a cryopreservation solution into stem cells, pipetting to disperse the stem cells to prepare a stem cell suspension, and placing the stem cell suspension on a freezing slide and cryopreserving it in liquid nitrogen (−196° C.).

According to an embodiment of the present invention, the thawing of the cryopreserved stem cells comprises placing According to the present invention, the compound of formula (I) has a structure shown as any one of the following:

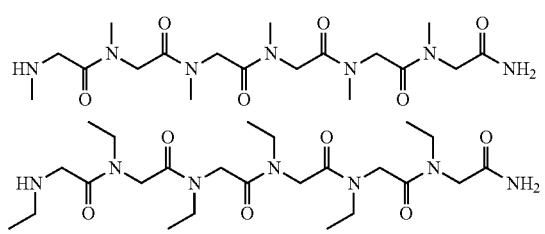

the freezing slide with the stem cells in an a-MEM medium and thawing the cells at 37° C.

According to an embodiment of the present invention, the stem cells are various stem cells that are known in the art and capable of differentiating, such as totipotent, pluripotent or unipotent stem cells, including but not limited to embryonic stem cells, various types of mesenchymal stem cells (e.g., umbilical cord mesenchymal stem cells, adipose mesenchymal stem cells and bone marrow mesenchymal stem cells), hematopoietic stem cells, and the like.

The present invention further provides a method of cryopreservation of organs and/or tissues, comprising: placing an organ and/or a tissue into a freezing equilibration solution for equilibration, placing the organ and/or the tissue into a cryopreservation solution, placing the organ and/or the tissue on a freezing slide, and cryopreserving it in liquid nitrogen.

In one embodiment, the organ and/or the tissue is an ovarian tissue or an ovarian organ, which may be a slice of the ovarian tissue or a complete ovarian tissue.

In the present invention, "cryopreservation" and "cryogenic preservation" have the same meaning and are used interchangeably, and refer to preservation of a substance, or a cell, a tissue, or an organ at a low temperature to retain the original physicochemical and/or biological activity, and physiological and biochemical functions thereof.

In the present invention, the type of "stem cells" is not particularly limited. The cryopreservation solution disclosed herein can be used for cryopreservation of various stem cells known in the art, including but not limited to umbilical cord mesenchymal stem cells, bone marrow mesenchymal stem cells, adipose mesenchymal stem cells, hematopoietic stem cells, and the like.

In the present invention, the biological tissue may be derived from animals, including warm-blooded mammals, such as humans and primates; birds; domestic or farm animals, such as cats, dogs, sheep, goats, cattle, horses and pigs; laboratory animals, such as mice, rats and guinea pigs; fish; reptiles; and zoo animals and wild animals, and the like.

Beneficial Effects

The cryopreservation solution and the freezing equilibration solution disclosed herein are free of DMSO, When used for cryopreservation of mouse oocytes and embryos, they can achieve cell and tissue survival rates and function expression stability same as or even higher than those of a commercial cryopreservation solution (comprising DMSO at a volume concentration of 15%), and thus they feature relatively high preservation efficiency. The DMSO-free and serum-free cryopreservation solution further solves the problems that the commercial cryopreservation solutions commonly used in clinical practice at present are poor in stability and prone to introduce parasitic biological contaminants due to the presence of serum. The cryopreservation solution disclosed herein features simple composition, readily available raw materials and low cost, and can be widely used in the cryopreservation of oocytes, cell-like cells (such as embryos), stem cells, tissues and organs.

DETAILED DESCRIPTION

Figure 1:
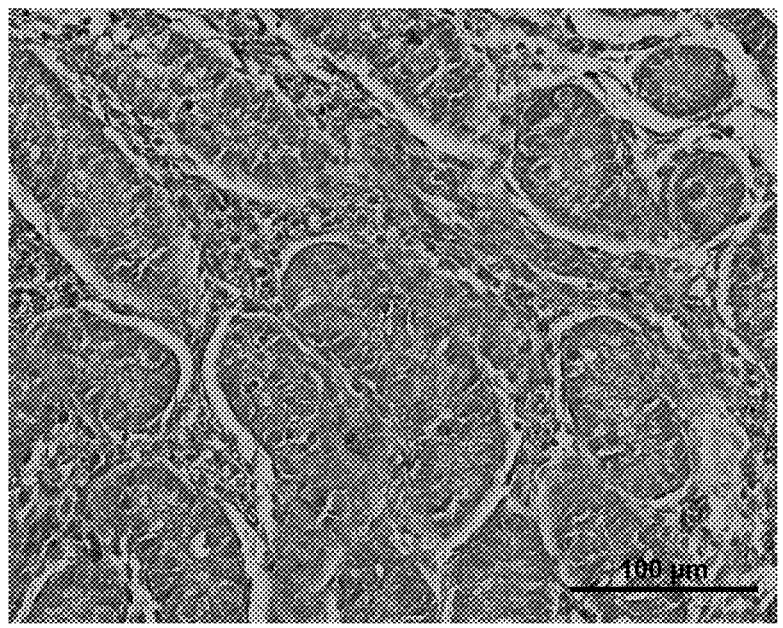
FIG. 1 is a picture of a stained slice of a fresh (unfrozen) ovarian organ of a 3-day newborn mouse.

The preparation method of the present invention will be further illustrated in detail with reference to the following specific examples. It should be understood that the following examples are merely exemplary illustration and explanation of the present invention, and should not be construed as limiting the protection scope of the present invention. All techniques implemented based on the aforementioned contents of the present invention are encompassed within the protection scope of the present invention.

Unless otherwise stated, the experimental methods used in the following examples are conventional methods. Unless otherwise stated, the reagents, materials, and the like used in the following examples are commercially available.

The PVA used in the examples of the present invention has a syndiotacticity of 50%-55%, a molecular weight of 13-23 kDa and a degree of hydrolysis of 98%.

In the examples of the present invention, poly-L-proline used in the freezing solution has a degree of polymerization of 8 or 15 and a molecular weight of 795 or 1475, and poly-L-arginine used has a degree of polymerization of 8 and a molecular weight of 1267. Poly-L-proline in a thawing solution has a degree of polymerization of 8 and a molecular weight of 795.

The survival rate in the examples of the present invention is the average survival rate of 3-12 repeated experiments.

Example 1. Cryopreservation of Mouse Oocytes and Embryos

1. Preparation of cryopreservation solutions: the cryopreservation solutions were prepared according to the following formulations A cryopreservation solution A comprises, per 100 mL, the following components:

| Substances | Content |
| --- | --- |
| Poly-L-proline (g) | 1.5 |
| PVA (g) | 2.0 |
| Ethylene glycol (mL) | 10 |
| Sucrose (mol · L$^{-1}$) | 0.5 |
| DPBS (mL) | Balance |

2.0 g of a PVA was dissolved in 25 mL of DPBS in a water bath at 80° C. by heating magnetic stirring, and the pH was adjusted to 7.0 to give a solution 1; 1.5 g of poly-L-proline was ultrasonically dissolved in another 20 mL of DPBS, and the pH was adjusted to 7.0 to give a solution 2; 17 g (0.05 mol) of sucrose (the final concentration of the sucrose in the cryopreservation solution was 0.5 mol $L^{-1}$) was ultrasonically dissolved in 25 mL of DPBS, and after the sucrose was completely dissolved, 10 mL of ethylene glycol was added to give a solution 3; after returning to room temperature, the solution 1, the solution 2 and the solution 3 were well mixed, the pH was adjusted to 7.0, and the volume was made up to a total volume of 100 mL using DPBS to give the cryopreservation solution A for later use.

A cryopreservation solution B comprises, per 100 mL, the following components:

| Substances | Content |
| --- | --- |
| L-Arg (g) | 8.0 |
| L-Thr (g) | 4.0 |
| PVA (g) | 2.0 |
| Ethylene glycol (mL) | 10 |
| Sucrose (mol · $L^{-1}$) | 0.5 |
| Fetal bovine serum (mL) | 20 |
| DPBS (mL) | Balance |

Steps of preparing the cryopreservation solution B: 2.0 g of a PVA was dissolved in 20 mL of DPBS in a water bath at 80° C. by heating and magnetic stirring, and the pH was adjusted to 7.1 to give a solution 1; 8.0 g of L-Arg and 4.0 g of L-Thr were dissolved in 20 mL of DPBS, and the pH was adjusted to 7.1 to give a solution 2; 17 g (0.05 mol) of sucrose (the final concentration of the sucrose in the cryopreservation solution was 0.5 mol $L^{-1}$) was ultrasonically dissolved in 20 mL of DPBS, and after the sucrose was completely dissolved, 10 mL of ethylene glycol was added to give a solution 3; after returning to room temperature, the solution 1, the solution 2 and the solution 3 were well mixed, the pH value was adjusted to 7.1, and the volume was made up to 80% of the total volume with DPBS; 20 mL of serum was added when the cryopreservation solution was used.

A cryopreservation solution C comprises, per 100 mL, the following components:

| Substances | Content |
| --- | --- |
| PVA (g) | 2.0 |
| Ethylene glycol (mL) | 10 |
| Sucrose (mol · $L^{-1}$) | 0.5 |
| Fetal bovine serum (mL) | 20 |
| DPBS (mL) | Balance |

2.0 g of a PVA was dissolved in 25 mL of DPBS in a water bath at 80° C. by heating magnetic stirring, and the pH was adjusted to 6.9 to give a solution 1; 17 g (0.05 mol) of sucrose (the final concentration of the sucrose in the cryopreservation solution was 0.5 mol $L^{-1}$) was ultrasonically dissolved in 25 mL of DPBS, and after the sucrose was completely dissolved, 10 mL of ethylene glycol was added to give a solution 2; after returning to room temperature, the solution 1 and the solution 2 were well mixed, the pH was adjusted, and the volume was made up to 80% of the total volume; 20 mL of serum was stored separately and added when the cryopreservation solution was used.

A cryopreservation solution D comprises, per 100 mL, the following components:

| Substances | Content |
| --- | --- |
| PVA (g) | 7.0 |
| Ethylene glycol (mL) | 10 |
| Sucrose (mol · $L^{-1}$) | 0.5 |
| DPBS (mL) | Balance |

2.0 g of a PVA was dissolved in 30 mL of DPBS in a water bath at 80° C. by heating and magnetic stirring, and the pH was adjusted to 7.0 to give a solution 1; 17 g (0.05 mol) of sucrose (the final concentration of the sucrose in the cryopreservation solution was 0.5 mol $L^{-1}$) was ultrasonically dissolved in 25 mL of DPBS, and after the sucrose was completely dissolved, 10 mL of ethylene glycol was added to give a solution 2; after returning to room temperature, the solution 1 and the solution 2 were well mixed, the pH was adjusted, and the volume was made up to a total volume of 100 mL to give the cryopreservation solution D for later use.

2. Preparation of freezing equilibration solutions: the freezing equilibration solutions were prepared according to the following formulations Freezing equilibration solution a: 2.0 g of a PVA was dissolved in 50 mL of DPBS in a water bath at 80° C. by heating magnetic stirring, the pH was adjusted to 7.0 after the PVA was completely dissolved, 7.5 mL of ethylene glycol was added, all the components were well mixed, and the volume was made up to 100 mL with DPBS to give the freezing equilibration solution a for later use. Freezing equilibration solution b (total volume: 100 mL): 7.5 mL of ethylene glycol was dissolved in 72.5 mL of DPBS and well mixed, and 20 mL of serum was added when the freezing equilibration solution was used.

Comparative Example 1

A freezing equilibration solution 1# comprises, per 1 mL, 7.5% (v/v) of DMSO, 7.5% (v/v) of ethylene glycol, 20% (v/v) of fetal bovine serum and the balance of DPBS.

A cryopreservation solution 1# comprises, per 1 mL, 15% (v/v) of DMSO, 15% (v/v) of ethylene glycol, 20% (v/v) of fetal bovine serum, 0.5 M sucrose and the balance of DPBS.

Freezing equilibration solution b comprises, per 1 mL, 7.5% (v/v) of ethylene glycol, 20% (v/v) of fetal bovine serum and the balance of DPBS.

A cryopreservation solution 2# comprises, per 1 mL, 10% (v/v) of ethylene glycol, 20% (v/v) of fetal bovine serum, 0.5 M sucrose and the balance of DPBS.

The three formulations of the thawing solutions used in the Example 1 and Comparative Example 1 disclosed herein were as follows:

A thawing solution 1# comprises a thawing solution I (comprising sucrose at 1.0 mol $L^{-1}$, 20% of serum, and the balance of DPBS), a thawing solution II (comprising sucrose at 0.5 mol $L^{-1}$, 20% of serum, and the balance of DPBS), a thawing solution III (comprising sucrose at 0.25 mol $L^{-1}$, 20% of serum, and the balance of DPBS), and a thawing solution IV (20% of serum, and the balance of DPBS).

A thawing solution 2# comprises a thawing solution I (comprising sucrose at 1.0 mol·$L^{-1}$, a PVA at 20 mg·$mL^{-1}$ and the balance of DPBS), a thawing solution II (comprising sucrose at 0.5 mol·$L^{-1}$, a PVA at 20 mg·$mL^4$ and the balance of DPBS), a thawing solution III (comprising sucrose at 0.25 mol·L$^{-1}$, a PVA at 20 mg mL$^{-1}$ and the balance of DPBS), and a thawing solution IV (comprising a PVA at 20 mg·mL$^{-1}$ and the balance of DPBS).

A thawing solution 3# comprises a thawing solution I (comprising sucrose at 1.0 mol L$^{-1}$, a PVA at 20 mg polyproline at 10 mg mL$^{-1}$, and the balance of DPBS), a thawing solution II (comprising sucrose at 0.5 mol L$^{-1}$, a PVA at 20 mg mL$^{-1}$, polyproline at 5.0 mg mL$^{-1}$, and the balance of DPBS), a thawing solution III (comprising sucrose at 0.25 mol mL$^{-1}$, a PVA at 20 mg mL$^{-1}$, polyproline at 2.5 mg mL$^{-1}$, and the balance of DPBS), and a thawing solution IV (a PVA at 20 mg mL$^{-1}$ and the balance of DPBS).

Application Example 1

The freezing equilibration solutions and the cryopreservation solutions of the example and comparative example described above were used to cryopreserve oocytes and embryos according to the schemes in Table 1 and. Table 2, respectively.

1. Cryopreservation of Oocytes

Mouse oocytes were firstly equilibrated in a freezing equilibration solution for 5 min, and then equilibrated in the prepared cryopreservation solution for 1 min. The oocytes equilibrated in the cryopreservation solution were loaded onto straws, and the straws were quickly put into liquid nitrogen (−196° C.) and then closed for cryopreservation. At the time of thawing, the cryopreserved oocytes were equilibrated in the thawing solution I at 37° C. for 5 min, and then equilibrated in the thawing solutions II-IV in sequence for 3 min each. After the thawed oocytes were incubated for 21 h, the number of the survived cells was observed, and the survival rates were calculated (see Table 1).

2. Cryopreservation of Embryos

Mouse embryos were firstly equilibrated in a freezing equilibration solution for 5 min, and then equilibrated in the prepared cryopreservation solution for 50 s. The embryos equilibrated in the cryopreservation solution were loaded onto straws, and the straws were quickly put into liquid nitrogen (−196° C.) and closed for cryopreservation. At the time of thawing, the frozen embryos were equilibrated in the thawing solution I at 37° C. for 3 min, and then equilibrated in the thawing solutions II-IV in sequence for 3 min each. After the thawed embryos were incubated for 2 h, the number of survived embryos was observed, and the survival rates were calculated (see Table 2).

TABLE 1

Survival rates of cryopreserved mouse oocytes

| No. | Equilibration solution | Cryopreservation solution | Thawing solution | Total number of frozen oocytes | Survival rates after 2 h |
|---|---|---|---|---|---|
| Application Embodiment 1 | a | A | Thawing solution 1# | 39 | 89.7% |
| Application Embodiment 2 | a | A | Thawing solution 3# | 60 | 98.6% |
| Application Embodiment 3 | b | B | Thawing solution 1# | 109 | 94.8% |
| Application Embodiment 4 | b | C | Thawing solution 1# | 90 | 97.7% |
| Application Embodiment 5 | a | D | Thawing solution 1# | 50 | 93.4% |
| Application Embodiment 6 | a | D | Thawing solution 2# | 53 | 96.5% |
| Comparative Embodiment 1 | Equilibration solution 1# | Freezing solution 1# | Thawing solution 1# | 146 | 95 |
| Comparative Embodiment 2 | b | Freezing solution 2# | Thawing solution 1# | 96 | 81.9% |

TABLE 2

Survival rates of cryopreserved mouse embryos

| No. | Equilibration solution | Cryopreservation solution | Thawing solution | Total number of frozen embryos | Survival rates after 2 h |
|---|---|---|---|---|---|
| Application Embodiment 7 | a | A | Thawing solution 1# | 42 | 95.2% |
| Application Embodiment 8 | a | D | Thawing solution 1# | 41 | 95.8% |
| Comparative Embodiment 3 | Equilibration solution 1# | Freezing solution 1# | Thawing solution 1# | 38 | 94.3% |
| Comparative Embodiment 4 | b | Freezing solution 2# | Thawing solution 1# | 39 | 82.4% |

According to the data of each of Example 1 and Comparative Example 1, it can be seen that although no DMSO is added, the DMSO-free cryopreservation solution and freezing equilibration solution disclosed herein, through the synergy of all the components, still have good cryopreservation effects on oocytes and embryos, and overcome the defect that existing cryopreservation solutions are toxic to cells or embryos due to the addition of DMSO at a relatively high concentration. Moreover, as can be seen from Application Embodiments 2 and 6-8, when the equilibration solution, the freezing solution and the thawing solution all are free of serum and DMSO, the survival rates of cryopreserved oocytes and embryos can be superior to those of existing commercial cryopreservation solutions under the combined action of the biomimetic ice growth inhibition material disclosed herein, a permeable protectant, namely ethylene glycol, and the like. The problems are further solved that the commercial cryopreservation solutions commonly used in clinical practice at present are short in shelf life and prone to introduce parasitic biological contaminants due to the presence of serum.

Example 2. Cryopreservation of Human Umbilical Cord Mesenchymal Stem Cells

1. Preparation of cryopreservation solutions: cryopreservation solutions were prepared according to the following formulations.

A cryopreservation solution E (total volume: 100 mL) comprises 10 mL of ethylene glycol, 20 mL of serum, 17 g of sucrose (0.5 mol $L^{-1}$), 4.0 g of poly-L-arginine (with a degree of polymerization of 8), 1.0 g of a PVA, and the balance of DPBS.

A cryopreservation solution F (total volume: 100 mL) comprises 20 mL of ethylene glycol, 20 mL of serum, 17 g of sucrose (0.5 mol $L^{-1}$), 16 g of L-Arg, 8.0 g of L-Thr, and the balance of DPBS.

A cryopreservation solution G (total volume: 100 mL) comprises 10 mL of ethylene glycol, 20 mL of serum, 17 g of sucrose (0.5 mol $L^{-1}$), 2.0 g of a PVA, and the balance of DPBS.

A cryopreservation solution H (total volume: 100 mL) comprises 10 mL of ethylene glycol, 20 mL of serum, 17 g of sucrose (0.5 mol $L^{-1}$), 28 g of TR, and the balance of DPBS.

A cryopreservation solution I (total volume: 100 mL) comprises 10 mL of ethylene glycol, 17 g of sucrose (0.5 mol $L^{-1}$), 2.0 g of a PVA, and the balance of DPBS.

The formulating methods of the cryopreservation solutions were same as those in Example 1.

A method of preparing TR is as follows:

(1) 2-chlorotrityl chloride resin was placed into a reaction tube, and added with DCM (20 mL·$g^{-1}$). The resulting mixture was shaken for 30 min. With the use of a sand-core funnel, the solvent was removed with suction. The residue was added with a three-fold molar excess of Fmoc-L-Thr (tBu)-OH and an eight-fold molar excess of DIEA, and finally added with DMF to dissolve. The resulting mixture was shaken for 30 min, Methanol was used for end-capping for 30 min.

(2) The solvent MIT was removed. 20% piperidine/DMF solution (10 mL·$g^{-1}$) was added, and the solvent was removed after 5 min; 20% piperidine/DMF solution (10 mL·$g^{-1}$) was added again, and the piperidine solution was removed after 15 min. A small amount of resin was taken and washed with ethanol three times, added with a ninhydrin reagent, and heated at 105-110° C. for 5 min. The color turned dark blue, which suggested a positive reaction.

(3) After the product obtained by the above reaction was sequentially washed with DMF (15 mL·$g^{-1}$, twice), methanol (15 mL·$g^{-1}$, twice) and DMF (15 mL·$g^{-1}$, twice), a two-fold excess of Fmoc-Arg(Pbf)-OH that was dissolved in as small an amount of DMF as possible was added to a reaction tube; a two-fold excess of HBTU was added. Immediately thereafter, an eight-fold excess of DIEA was added and reacted for 30 min.

(4) After the solution was removed with suction, a small amount of resin was taken and washed with ethanol three times, added with a ninhydrin reagent, and heated at 105-110° C. for 5 min. The colorless mixture suggested a negative reaction, that is, the reaction was complete.

(5) After the product obtained by the above reaction was sequentially washed with DMF (15 mL·$g^{-1}$, twice), methanol (15 mL·$g^{-1}$, twice) and DMF (15 mL·$g^{-1}$, twice), the solvent was removed. 20% piperidine/DMF solution (10 mL·$g^{-1}$) was added, and the solvent was removed after 5 min; 20% piperidine/DMF solution (10 mL·$g^{-1}$) was added again, and the piperidine solution was removed after 15 min. A small amount of resin was taken and washed with ethanol, added with a ninhydrin reagent, and heated at 105-110° C. for 5 min. The color turned dark blue, which suggested a positive reaction.

(6) After the product obtained by the above reaction was sequentially washed with DMF (15 mL·$g^{-1}$, twice), methanol (15 mL·$g^{-1}$, twice) and DCM (15 mL·$g^{-1}$, twice), the resin was dried with suction.

(7) The product was cut using a cleaving liquid (15 mL·$g^{-1}$, TFA:water:EDT:Tis=95:1:2:2, v/v) for 90 min. The cleaving liquid was blown to dryness with nitrogen, and then lyophilized to give a crude product of polypeptide.

(8) The polypeptide was purified by HPLC and subjected to salt-conversion or desalting. HPLC: tR=4.8 mins (purification column model: Kromasil 100-5C18, 4.6 mm*250 mm; gradient eluent: acetonitrile with 0.1% TFA and aqueous solution with 0.1% TFA, 0 mins-1:99, 20 mins-1:4). The purified solution was lyophilized to give a finished product L-Thr-L-Arg (TR). The yield was about 80%. The mass spectrum presents $[M+H]^+$ at 276.2.

Comparative Example 2

A cryopreservation solution 3# comprises, per 1 mL: 10% (v/v) of DMSO, 15% (v/v) of fetal bovine serum, and the balance of a-MEM medium (C12571500BT, Invitrogen, USA).

Human umbilical cord mesenchymal stem cells were cryopreserved using the cryopreservation solutions described above according to the scheme in Table 3. The cryopreservation method of the human umbilical cord stem cells is specifically a microdroplet method, namely: human umbilical cord mesenchymal stem cells on a culture dish were digested using 25% pancreatin for 2 min, put into a culture solution (10% FBS+a-MEM culture medium) of the same volume, and gently pipetted until the stem cells completely fell off; the cells were added into a 1.5 mL, centrifuge tube for centrifuging for 5 min at 1000 rpm, and the supernatant was discarded to separate the cells from the culture medium; 10 μL of freezing solution was added to the bottom of the centrifuge tube, the stem cells were gently pipetted to disperse stem cell dusters, and 10 μL of freezing solution with the stem cells was placed on a freezing slide and then cryopreserved in liquid nitrogen (−196° C.). At the time of thawing, the freezing slide with the cells and the freezing solution was placed directly in the a-MFM medium at 37° C. for thawing. After thawing, cells were stained with trypan blue to observe the survival rates, and the number of cells was counted using an instrument JIMBIO-FIL, survival rate=number of live cells/total number of cells (see Table 3).

TABLE 3

Survival rates of cryopreserved human umbilical cord mesenchymal stem cells

| No. | Cryopreservation solution | Cryopreservation method | Survival rates |
|---|---|---|---|
| Application Embodiment 9 | Cryopreservation solution E | Microdroplet method | 92.4% |
| Application Embodiment 10 | Cryopreservation solution F | Microdroplet method | 71.0% |
| Application Embodiment 11 | Cryopreservation solution G | Microdroplet method | 72.2% |
| Application Embodiment 12 | Cryopreservation solution H | Microdroplet method | 75.1% |
| Application Embodiment 13 | Cryopreservation solution I | Microdroplet method | 77.1% |
| Comparative Embodiment 5 | Cryopreservation solution 3# | Microdroplet method | 76.6% |
| Comparative Embodiment 6 | Cryopreservation solution 1# | Microdroplet method | 63.9% |

When the cryopreservation solution disclosed herein is used for cryopreservation of the human umbilical cord mesenchymal stem cells, the survival rate of the stem cells can reach 92.4% (Application Embodiment 9) although no DMSO is added and can reach 77.1% (Application Embodiment 13) even when no DMSO and serum are added. This means that the cryopreservation reagent can achieve the same effectiveness as a conventional freezing solution in freezing stem cells, and has a post-thaw survival rate even far higher than that of a cryopreservation solution (Comparative Embodiment 5) comprising 10% of DMSO commonly used at present, and the cryopreservation effect of the PVA-based cryopreservation solution is remarkably superior to that of Comparative Embodiment 6 without PVA.

Example 3. Cryopreservation of Intact Ovarian Organs and Ovarian Tissue Slices A cryopreservation solution J (total volume: 100 mL) comprises 10 mL of ethylene glycol, 17 sucrose (0.5 mol $L^{-1}$), 2.0 of a PVA, and the balance of DPBS.

A cryopreservation solution K (total volume: 100 mL) comprises 10 mL of ethylene glycol, 20 mL of serum, 17 g of sucrose (0.5 mol $L^{-1}$), 1.0 g of a PVA, and the balance of DPBS.

A cryopreservation solution L comprises 10 mL of ethylene glycol, 20 mL of serum, 17 g of sucrose (0.5 mol $L^{-1}$), 4.0 g of poly L-arginine (with a degree of polymerization of 8), 1.0 g of a PVA, and the balance of DPBS.

Comparative Example 3: a cryopreservation solution comprises, per 1 mL, 15% (v/v) of DMSO, 15% (v/v) of ethylene glycol, 20% (v/v) of serum, 0.5 M sucrose, and the balance of DPBS.

Freezing equilibration solution a: 2.0 g of a PVA was dissolved in 50 mL of DPBS in a water bath at 80° C. by heating magnetic stirring, the pH was adjusted to 7.0 after the PVA was completely dissolved, 7.5 mL of ethylene glycol was added, all the components were well mixed, the pH was adjusted, and the volume was made up to 100 mL to give the freezing equilibration solution a for later use.

Freezing equilibration solution b: 7.5 mL of ethylene glycol was added into 72.5 mL of DPBS and well mixed, and 20 mL of serum was added when the freezing equilibration solution was used.

Comparative Example 3

A freezing equilibration solution 14 comprises, per 1 mL, 7.5% (v/v) of DMSO, 7.5% (v/v) of ethylene glycol, 20% (v/v) of fetal bovine serum and the balance of DPBS.

A cryopreservation solution 14 comprises, per 1 mL: 15% (v/v) of DMSO, 15% (v/v) of ethylene glycol, 20% (v/v) of fetal bovine serum, sucrose at 0.5 mol $L^{-1}$, and the balance of DPBS.

A thawing solution 14 comprises a thawing solution I (comprising sucrose at 1.0 mol $L^{-1}$, 20% of serum and the balance of DPBS), a thawing solution II (comprising sucrose at 0.5 mol $L^{-1}$, 20% of serum and the balance of DPBS), a thawing solution III (comprising sucrose at 0.25 mol $L^{-1}$, 20% of serum and the balance of DPBS), and a thawing solution IV (comprising 20% of serum and the balance of DPBS).

A thawing solution 2# comprises a thawing solution I (comprising sucrose at 1.0 mol $L^{-1}$; a PVA at 20 mg·$mL^{-1}$ and the balance of DPBS), a thawing solution II (comprising sucrose at 0.5 mol·$L^{-1}$, a PVA at 20 mg·$mL^{-1}$ and the balance of DPBS), a thawing solution III (comprising sucrose at 0.25 mol·$L^{-1}$, a PVA at 20 mg $mL^{-1}$ and the balance of DPBS), and a thawing solution IV (comprising a PVA at 20 mg·$mL^{-1}$ and the balance of DPBS).

The intact ovarian organs of mice newly born within 3 days and the ovarian tissue slices of sexually mature mice were cryopreserved using the cryopreservation solutions described above and the freezing equilibration solutions and cryopreservation solutions of the comparative example according to the schemes in Table 4 and Table 5.

The whole ovarian organs or ovarian tissue slices were firstly equilibrated in an equilibration solution at room temperature for 25 min, then equilibrated in the prepared cryopreservation solution for 15 min, and then loaded onto straws; the straws were put into liquid nitrogen for preservation. After thawing, the intact ovarian organs or ovarian tissue slices were incubated in a culture solution (10% FBS+a-MEM) in an incubator at 37° C./5% $CO_2$ for 2 h for further thawing, and then fixed with 4% paraformaldehyde, embedded in paraffin and stained with HE for morphological observation. The results are shown in FIGS. 1-10. FIG. 1 is a picture of a slice of a fresh unfrozen ovarian organ, and FIG. 6 is a picture of a slice of a fresh unfrozen ovarian tissue.

TABLE 4

Ovarian organ cryopreservation scheme

Figure 2:
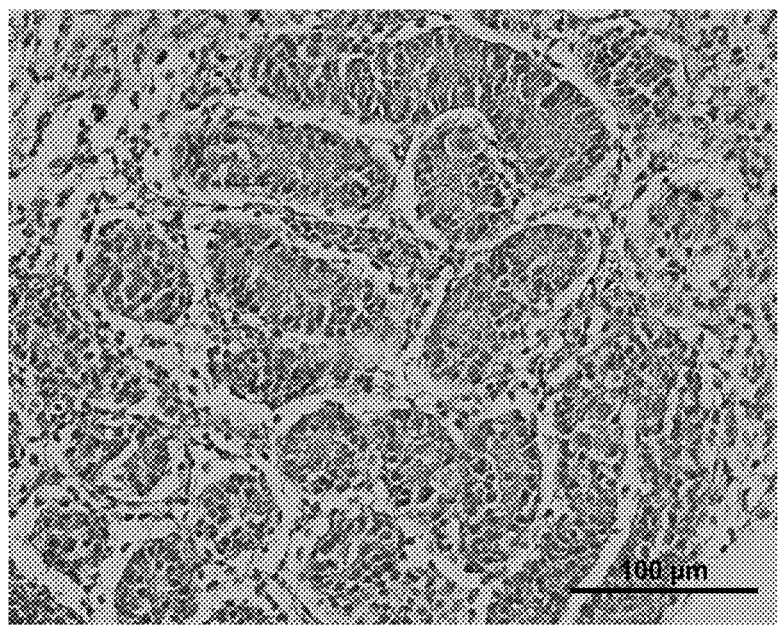
FIG. 2 is a picture of a stained slice of the cryopreserved intact ovarian organ of Comparative Embodiment 7 after thawing.
Figure 3:
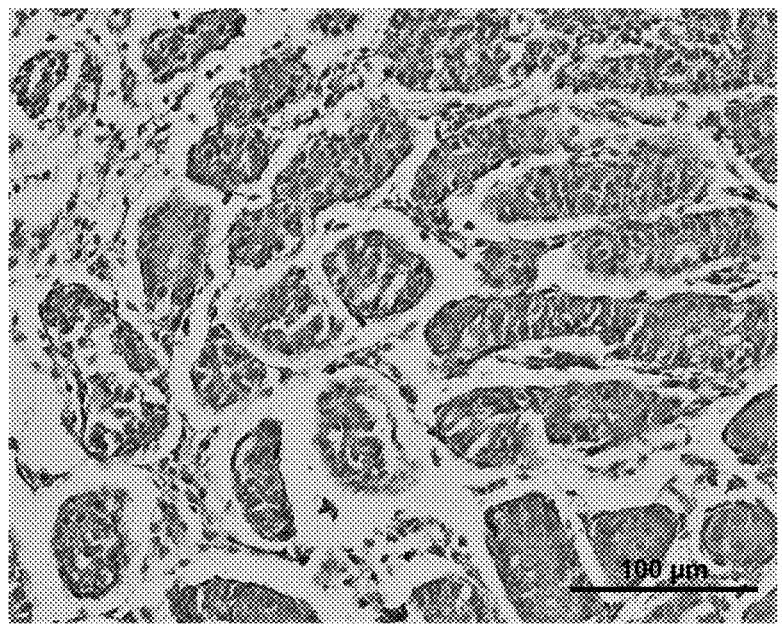
FIG. 3 is a picture of a stained slice of the cryopreserved intact ovarian organ of Application Embodiment 14 after thawing.
Figure 4:
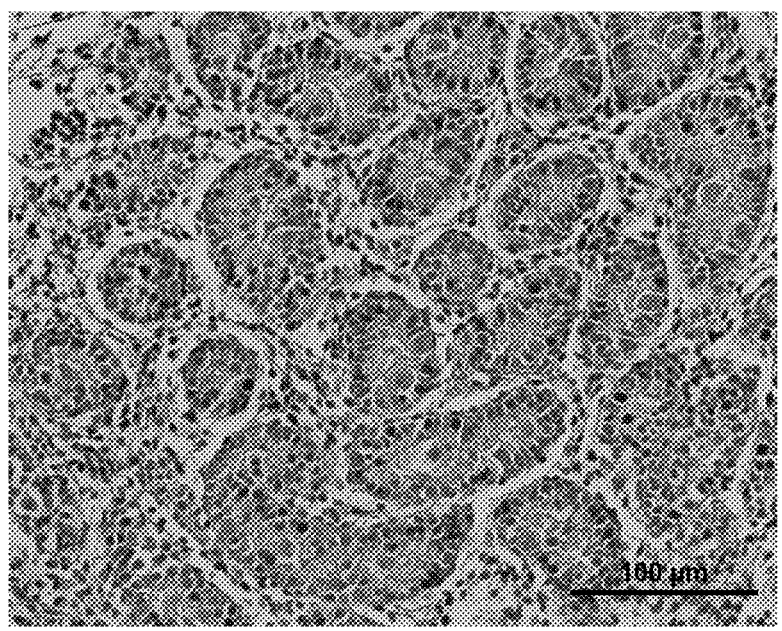
FIG. 4 is a picture of a stained slice of the cryopreserved intact ovarian organ of Application Embodiment 15 after thawing.
Figure 5:
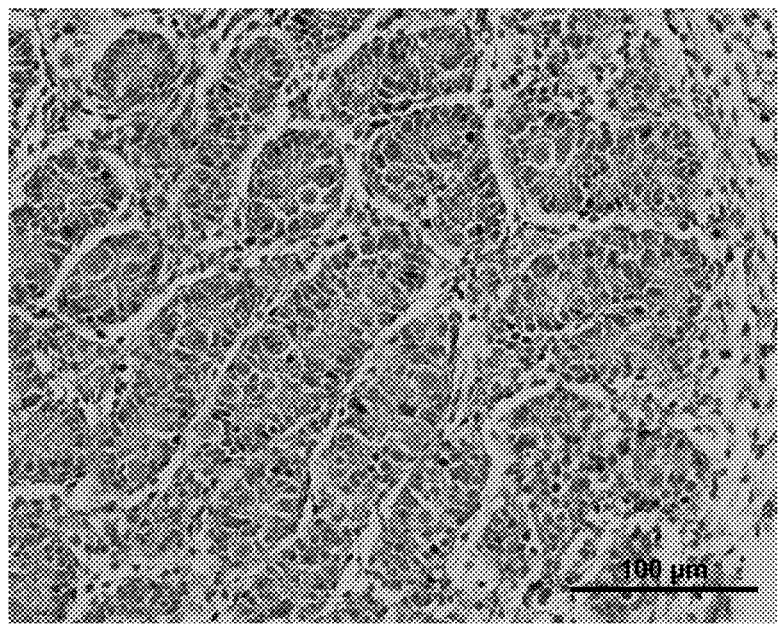
FIG. 5 is a picture of a stained slice of the cryopreserved ovarian organ of Embodiment 16 after thawing.
Figure 6:
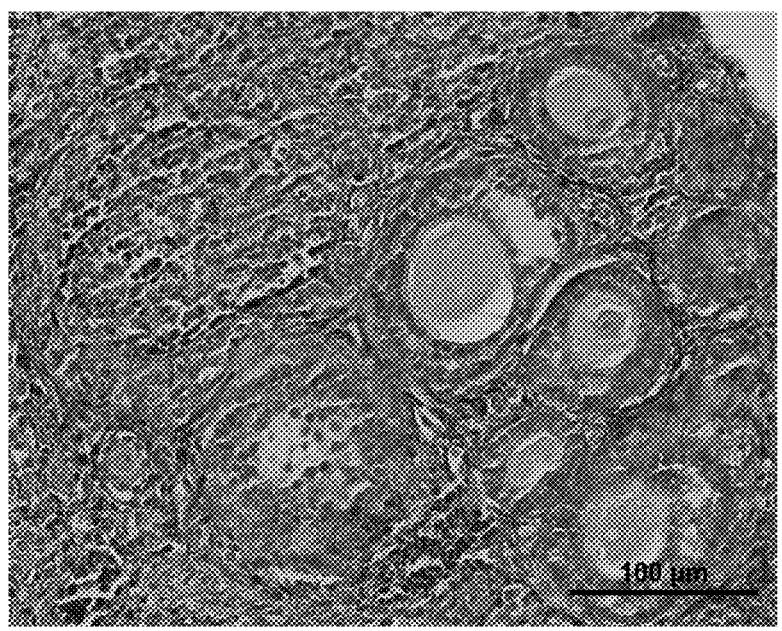
FIG. 6 is a picture of a stained slice of fresh (unfrozen) ovarian tissue of a sexually mature mouse.

| No. | Equilibration solution | Cryopreservation solution | Thawing solution | Morphology |
|---|---|---|---|---|
| Application Embodiment 14 | a | J | Thawing solution 2# | FIG. 3 |
| Application Embodiment 15 | b | K | Thawing solution 1# | FIG. 4 |
| Application Embodiment 16 | b | L | Thawing solution 1# | FIG. 5 |
| Comparative Embodiment 7 | Equilibration solution 1# | Freezing solution 1# | Thawing solution 1# | FIG. 2 |

TABLE 5

Ovarian tissue cryopreservation scheme

Figure 8:
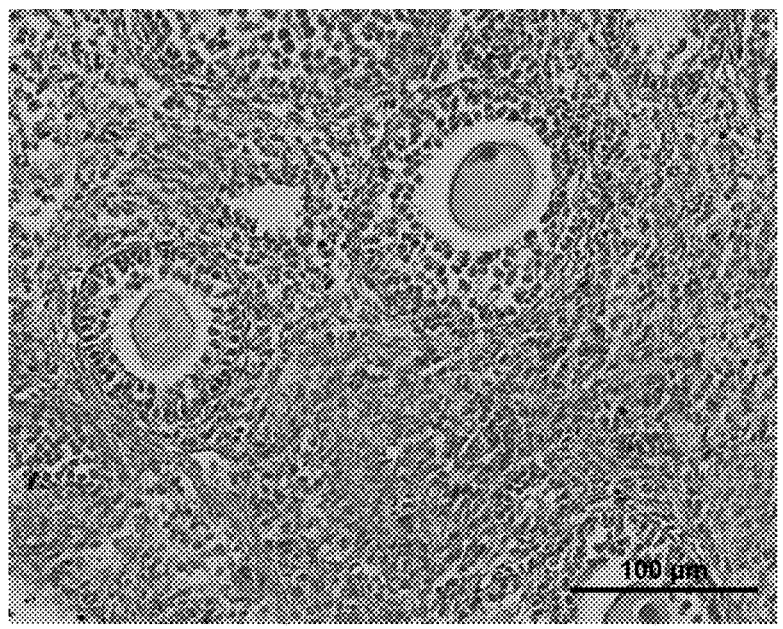
FIG. 8 is a picture of a stained slice of the cryopreserved ovarian tissue of Application Embodiment 17 after thawing.
Figure 9:
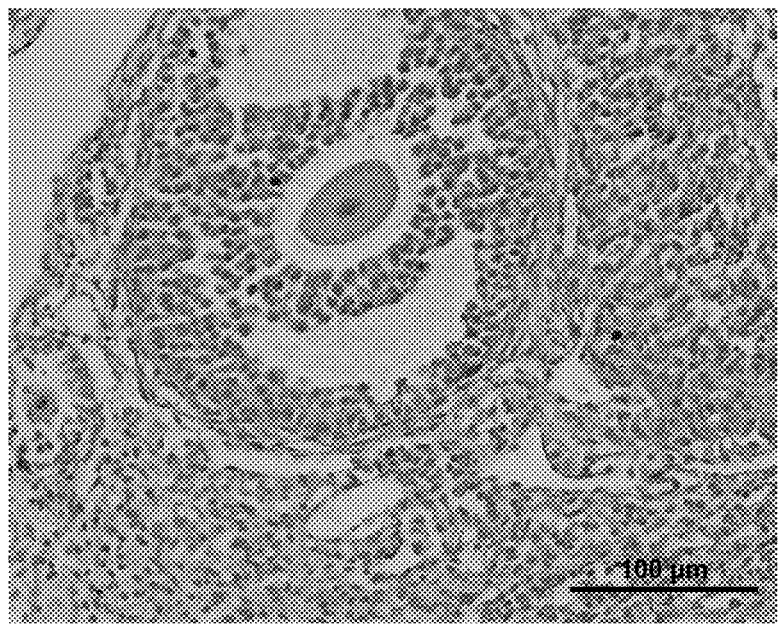
FIG. 9 is a picture of a stained slice of the cryopreserved ovarian tissue of Application Embodiment 18 after thawing.

| No. | Equilibration solution | Cryopreservation solution | Thawing solution | Morphology |
|---|---|---|---|---|
| Application Embodiment 17 | a | J | Thawing solution 2# | FIG. 8 |
| Application Embodiment 18 | b | K | Thawing solution 1# | FIG. 9 |

TABLE 5-continued

Ovarian tissue cryopreservation scheme

Figure 7:
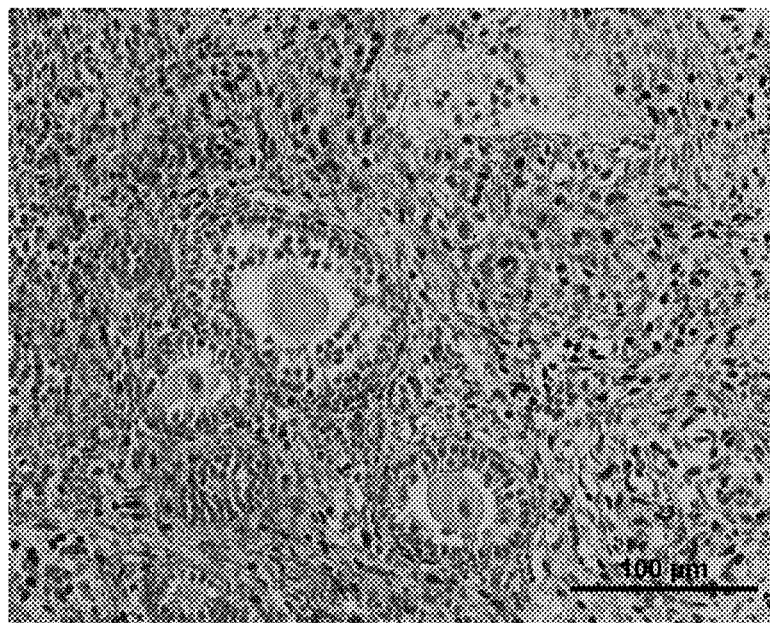
FIG. 7 is a picture of a stained slice of the cryopreserved ovarian tissue of Comparative Embodiment 8 after thawing.
Figure 10:
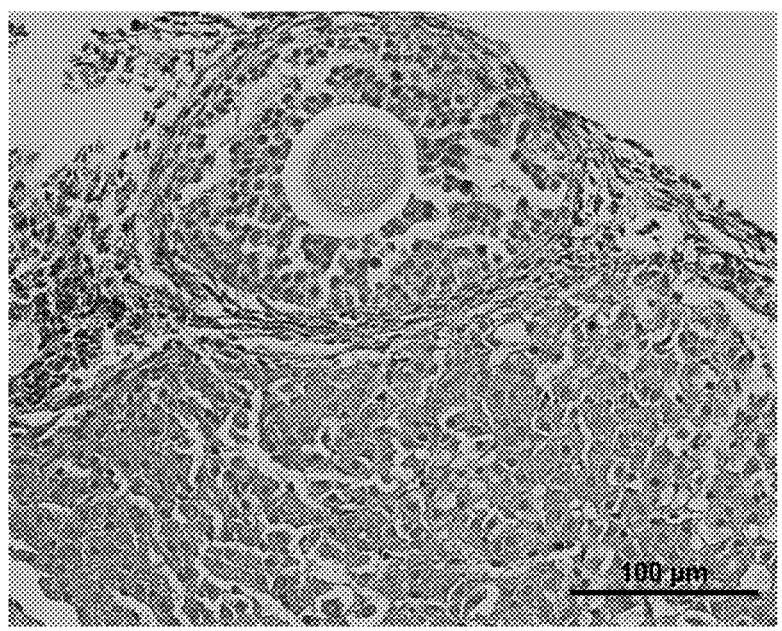
FIG. 10 is a picture of a stained slice of the cryopreserved ovarian tissue of Application Embodiment 19 after thawing.

| No. | Equilibration solution | Cryopreservation solution | Thawing solution | Morphology |
|---|---|---|---|---|
| Application Embodiment 19 | b | L | Thawing solution 1# | FIG. 10 |
| Comparative Embodiment 8 | Equilibration solution 1# | Freezing solution 1# | Thawing solution 1# | FIG. 7 |

As can be seen from FIGS. 1-5, compared with Comparative Embodiment 7 free of the amino acid biomimetic ice growth inhibition material and fresh unfrozen ovarian organs, Examples 14-16 are characterized in that: the original follicle structure is relatively intact, the interstitial structure is relatively intact, the cytoplasm of cells is homogeneous and lightly stained in a relatively large amount, and nucleus shrinkage and deep staining are relatively mild; the structure of the vascular wall is intact, lumen collapse is mild, the cytoplasm of endothelial cells is homogeneous and lightly stained in a relatively large amount, and nucleus shrinkage and deep staining are relatively mild. It can be seen that Examples 14-16 have better cryopreservation effect on ovarian organs.

As can be seen from FIGS. 6-10, as compared with Comparative Embodiment 8 and fresh unfrozen ovarian tissue, the schemes of Examples 17-19 are characterized in that: the antral follicle structure is relatively intact, the interstitial structure is relatively intact, the cytoplasm of cells is homogeneous and lightly stained in a relatively large amount, and nucleus shrinkage and deep staining are relatively mild. It can be seen that the cryopreservation solutions disclosed herein have better effect on cryopreservation of ovarian tissues than the prior art.

The examples of the present invention have been described above. However, the present invention is not limited to the above examples. Any modification, equivalent, improvement and the like made without departing from the spirit and principle of the present invention shall fall within the protection scope of the present invention.

The invention claimed is:

1. A DMSO-free cryopreservation solution, comprising, per 100 mL, 0.01-50 g of a biomimetic ice growth inhibition material, 5.0-45 ml of a polyalcohol, a water-soluble saccharide at 0.1-1.0 mol $L^{-1}$, 0-30 mL of serum and the balance of a buffer, wherein the biomimetic ice growth inhibition material is selected from an atactic polyvinyl alcohol (PVA) having a syndiotacticity of 15%-60% and a molecular weight of from great than 10 kDa to 500 kDa, or a combination of said PVA with an amino acid biomimetic ice growth inhibition material.

2. The cryopreservation solution according to claim 1, wherein the amino acid biomimetic ice growth inhibition material is selected from a polyamino acid with a degree of polymerization ≥2, an amino acid, a peptide compound, and mixtures thereof.

3. The cryopreservation solution according to claim 2, wherein the peptide compound is a polypeptide, a glycopeptide derivative, or a compound of formula (I):

$$R-N(H)-\left[C(H_2)-C(=O)-N\right]-\left[C(R)(H_2)-C(=O)-C-NH_2\right]_n$$

wherein R is selected from substituted or unsubstituted alkyl, and the substituent is selected from —OH, —NH$_2$, —COOH, and —CONH$_2$, and n is an integer greater than or equal to 1 and less than or equal to 1000.

4. The cryopreservation solution according to claim 3, wherein R is substituted or unsubstituted $C_{1-6}$ alkyl.

5. The cryopreservation solution according to claim 3, wherein R is —CH$_3$, —CH$_2$CH$_3$, or —CH$_2$CH$_2$COOH.

6. The cryopreservation solution according to claim 1, wherein the ice growth inhibition material is PVA, and the content of the PVA is 0.1-6.0 g.

7. The cryopreservation solution according to claim 1, wherein the ice growth inhibition material is a combination of the PVA and an amino acid, the PVA and a polyamino acid, and the PVA with a mixture of amino acid and polyamino acid.

8. The cryopreservation solution according to claim 7, wherein ice growth inhibition material consists of 0.1-5.0 g of the PVA, 8.0-35 g of the amino acid, and/or 1.0-9.0 g of the polyamino acid.

9. The cryopreservation solution according to claim 1, wherein the PVA has a syndiotacticity of 50%-60%.

10. The cryopreservation solution according to claim 9, wherein
the PVA is a PVA having a degree of hydrolysis of greater than 80%; and/or
the polyamino acid is selected from lysine, arginine, proline, threonine, histidine, glutamic acid, aspartic acid, glycine, and mixtures thereof; and/or
the polypeptide is a peptide consisting of 2 to 8 different amino acids; and/or
the glycopeptide derivative is synthesized by a saccharide and an amino acid.

11. The cryopreservation solution according to claim 10, wherein
the polypeptide is selected from L-Thr-L-Arg (TR), L-Thr-L-Pro (TP), L-Arg-L-Thr (RT), L-Pro-L-Thr (PT), L-Thr-L-Arg-L-Thr (TRT), L-Thr-L-Pro-L-Thr (TPT), L-Ala-L-Ala-L-Thr (AAT), and mixtures thereof; and/or
the glycopeptide derivative is selected from GDL-L-Thr, GDL-L-Gln, GDL-L-Asn, GDL-L-Phe, GDL-L-Tyr, GDL-L-Val, GDL-L-Ser, and mixtures thereof.

12. The cryopreservation solution according to claim 1, wherein the content of the polyalcohol is 6.0-28 mL; and/or
the content of serum is 0; and/or
the content of the water-soluble saccharide is 0.1-1.0 mol $L^{-1}$; and/or
the pH of the cryopreservation solution is 6.5-7.6.

13. The cryopreservation solution according to claim 12, wherein the polyalcohol is $C_{2-5}$ polyalcohol; and/or
the water-soluble saccharide is selected from a non-reducing disaccharide, a water-soluble polysaccharide, a glycoside, and mixtures thereof; and/or
the buffer is selected from DPBS, hepes-buffered HTF buffer, a cell buffer, and mixtures thereof and/or
the serum is human serum albumin or a substitute thereof for a human-derived cryopreservation object, or is fetal bovine serum or bovine serum albumin for a non-human-derived cryopreservation object.

14. The cryopreservation solution according to claim 13, wherein
the polyalcohol is ethylene glycol, propylene glycol, or glycerol; and/or
the water-soluble saccharide is selected from sucrose, water-soluble cellulose, trehalose, and polysucrose; and/or
the serum is sodium dodecyl sulfate.

15. A DMSO-free cryopreservation reagent comprising the cryopreservation solution according to claim 1 and a freezing equilibration solution, wherein the cryopreservation solution and the freezing equilibration solution are independently present; and the content of serum is 0, and the freezing equilibration solution comprises, per 100 mL, 0.5-2.5 g of a PVA, 7.5-15 mL of a polyalcohol and the balance of a buffer.

16. A preparation method of the cryopreservation solution according to claim 1, comprising: dissolving the ice growth inhibition material in the buffer, cooling to room temperature before adjusting the pH, dissolving other components in the rest buffer, and mixing after cooling.

17. The preparation method according to claim 16, wherein the preparation method comprises:
dissolving the PVA in a portion of the buffer and cooling to room temperature before adjusting the pH to form a solution 1;
optionally, dissolving the polyamino acid or amino acid in a portion of the buffer and cooling to room temperature before adjusting the pH to form a solution 2;
dissolving the water-soluble saccharide in a portion of the buffer and adding other components except serum after the water-soluble saccharide is completely dissolved to form a solution 3;
mixing the solution 1, optionally the solution 2 and the solution 3 after they are cooled to room temperature, and adjusting the pH and making up to a predetermined volume with the buffer to obtaining the cryopreservation solution; and
optionally, adding serum to the cryopreservation solution.

18. A method of cryopreservation of biological tissues comprising utilizing the cryopreservation solution according to claim 1 and a freezing equilibration solution, wherein the freezing equilibration solution comprises, per 100 mL, 0.5-2.5 g of a PVA, 7.5-15 mL of a polyalcohol and the balance of a buffer.

19. The method according to claim 18, wherein the biological tissue is selected from at least one of an oocyte, an embryo, a stem cell, and an organ and tissue.

20. The cryopreservation solution according to claim 18, wherein
the polypeptide is a dipeptide, a tripeptide, or a tetrapeptide; and/or
the glycopeptide derivative is a molecule consisting of gluconolactone (GDL) and an ice-philic amino acid through chemical bonding.

* * * * *